United States Patent [19]

Toth et al.

[11] Patent Number: 4,795,494

[45] Date of Patent: Jan. 3, 1989

[54] BEET JUICE PURIFICATION SYSTEM

[75] Inventors: Laszlo Toth, Thornton; Michael R. Conway, Evergreen Highlands, both of Colo.

[73] Assignee: The Western Sugar Company, Denver, Colo.

[21] Appl. No.: 167,845

[22] Filed: Mar. 14, 1988

[51] Int. Cl.[4] ...................... C07C 53/00; C07C 55/00; C13D 3/12

[52] U.S. Cl. ........................................ 127/48; 127/50; 127/55

[58] Field of Search .................... 127/58, 46.1, 48, 50, 127/55, 29, 42, 53; 426/48

[56] References Cited

U.S. PATENT DOCUMENTS 3,113,044 12/1963 Alston .................................. 127/48

3,734,773 5/1973 Haley .................................... 127/48

*Primary Examiner*—Marianne Cintins

*Attorney, Agent, or Firm*—Klaas & Law

[57] ABSTRACT

A process for the removal of non-sugar impurities from beet diffusion juice having essentially no beet tissue particles therein and comprising water, sugar, and dissolved and colloidal non-sugar impurities. The diffusion juice is subjected to a progressive preliming procedure to thereby produce a limed first juice fraction containing non-sugar flocs and a limed, floc-free second juice fraction. The fractions are separated and the floc-free fraction is subjected to cold and hot main liming. Subsequently, and without substantial mechanical or chemical degradation, at least a portion of the first juice fraction containing at least a portion of the non-sugar flocs is united with the main-limed second juice fraction in a first carbonation procedure wherein carbon dioxide reacts with the lime present to produce calcium carbonate precipitate which, in addition to being an adsorption filter aid, forms protective scales around the floc particles. The resulting single juice fraction is separated, further treated in a second carbonation procedure, and filtered for subsequent sugar crystallization.

10 Claims, 1 Drawing Sheet

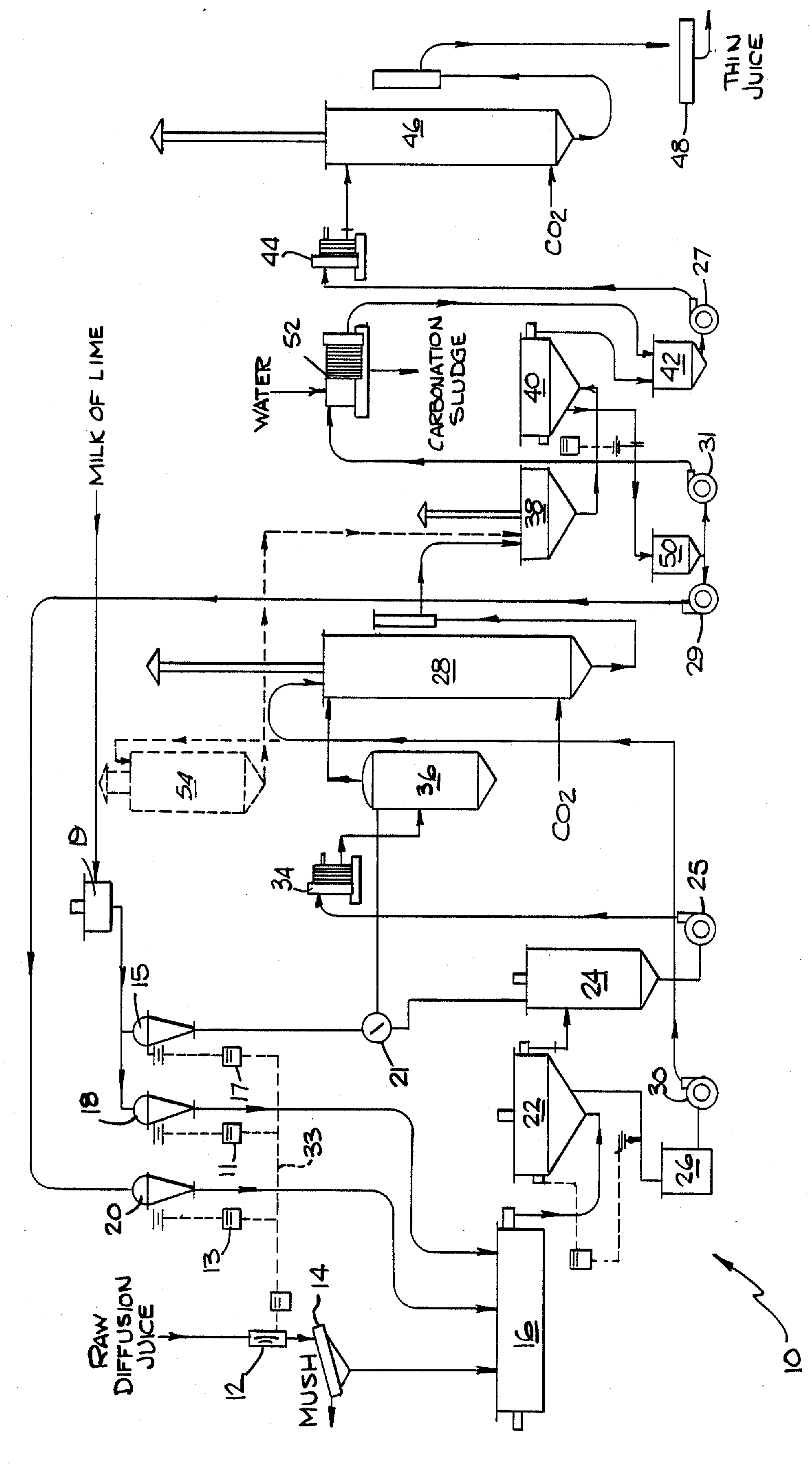
RAW DIFFUSION JUICE
MUSH
MILK OF LIME
WATER
CARBONATION SLUDGE
THIN JUICE
CO2
CO2
10
12
13
14
15
16
17
18
19
20
21
22
24
25
26
27
28
29
30
31
33
34
36
38
40
42
44
46
48
50
52
54
11

BEET JUICE PURIFICATION SYSTEM

BACKGROUND OF THE INVENTION

This invention relates generally to the purification of beet juice for subsequent sugar production, and in particular to a process for the removal of non-sugar impurities from raw juice.

In a typical commercial sugar beet processing operation, juice from the beets is extracted by means of a conventional diffusion process. This juice normally contains a considerable amount of beet tissue particles, commonly termed "mush," and usually about 13-16% water-soluble materials. The mush is separated by means of mechanical screening, and the remaining diffusion juice is further processed for purification and consequent sugar production. Prior to such purification, diffusion juice comprises water, sugar and various dissolved and colloidal non-sugar impurities. Because these non-sugars are usually highly-colorized, thermally-unstable material, they severely interfere with both the quality and quantity of subsequently-produced sugar. It is therefore most important to remove as great a quantity of non-sugars as possible from the diffusion juice.

A typical current process for such purification begins with a progressive preliming step where the pH of the juice is gradually increased from about 6.5 to about 11.6 by means of lime addition and carbonation sludge addition. Since many of the non-sugars are proteins, this gradual pH increase enables them to reach their respective iso-electric points, at which time they flocculate. After preliming, the resultant juice-floc-lime mixture enters a cold main liming step (30°-40° C.) and a hot main liming step (80°-90° C.) where additional lime is added to increase the pH to a value above about 12.6. This procedure acts to decompose non-sugars not affected during the preliming step, and is said to thereby stabilize the juice. The resulting limed juice composition is then subjected to a first carbonation step wherein carbon dioxide gas is introduced to react with the lime and produce a large volume of fine calcium carbonate precipitate. This calcium carbonate acts to adsorb some remaining dissolved non-sugars and additionally acts as a filter aid in the separation of prelimed flocs during settling in conventional sludge thickeners and during additional filtering. Finally, the resultant juice composition is subjected to additional heating, a second carbonation step, and final filtering. The resultant effluent, termed "thin juice," is then ready for evaporative thickening and sugar crystallization.

Upon investigation of the above-described process, however, it has been found that certain flocs formed during the preliming steps are sensitive and are destroyed because of the harsh mechanical and chemical conditions present during the main liming step. This destruction occurs because of repeptization of some of the proteinaceous flocs or because of mechanical degradation, and consequently lowers the effect of prelimer non-sugar separation. It is therefore a primary object of the present invention to provide a juice purification process wherein the non-sugar flocs formed during preliming and which separate certain non-sugar impurities from the juice remain relatively undisturbed for the remainder of the juice purification process. In accord therewith, another object of the invention is to remove these prelimer flocs from the juice prior to main liming, yet reclaim minor, yet significant, quantities of juice accompanying the prelimer flocs for subsequent processing. It is yet another object of the invention to reclaim such accompanying juice by re-introducing the prelimer flocs and accompanying juice to the remaining juice during the carbonation step of the purification process whereby calcium carbonate scales surround and protect respective floc particles. These and other objects will become apparent throughout the description which follows.

SUMMARY OF THE INVENTION

The present invention is a process for the removal of non-sugar impurities from beet diffusion juice having essentially no beet tissue particles therein and comprising water, sugar, and dissolved and colloidal non-sugar impurities. The process comprises subjecting the diffusion juice to a progressive preliming procedure wherein lime and carbonation sludge are added to the juice to gradually increase the pH of the juice to about 11.6. This preliming procedure produces a limed first juice fraction, containing non-sugar flocs generally formed from proteinaceous non-sugar impurities which flocculate when respective iso-electric points are reached, and a limed second juice fraction. The first juice fraction containing the flocs is separated from the second juice fraction, and the latter is subjected to a main liming procedure. In this main liming procedure, lime is added to the second juice fraction and continuously intimately mixed therewith at an ambient temperature usually about 30°-40° C., generally termed "cold" main liming, to increase the pH above about 12.6. This condition is maintained for a period of time sufficient to degrade non-sugar impurities which are degradable at the stated temperature range. Thereafter, the temperature is increased to about 80°-90° C., generally termed "hot" main liming, while intimate mixing continues for a period of time sufficient to degrade non-sugar impurities which are degradable at the higher temperature.

Upon completion of the main liming procedure of the second juice fraction, all of the first juice fraction containing the flocs is preferably united in a first carbonation procedure with the second juice fraction. The first juice fraction is so united without substantial mechanical or chemical degradation of the flocs. In this first carbonation procedure, carbon dioxide gas is introduced in a quantity sufficient to react with at least about 95% of the lime present in the first and second juice fractions to thereby produce calcium carbonate precipitate and a single juice fraction. In addition to adsorbing certain remaining non-sugar impurities, the calcium carbonate precipitate also effectively insulates the non-sugar flocs by creating permanent calcium carbonate scales around each floc particle. These scales are surface active, and therefore attract remaining additional dissolved non-sugars as well as colorants to thereby aid in juice purification. The single juice fraction is separated from the precipitate and is further treated in a second carbonation procedure wherein the juice is heated to a temperature immediately below the boiling point of the juice and carbon dioxide gas is introduced in a quantity sufficient to react with any residual lime accompanying the juice. Calcium carbonate precipitate is again formed by reacting with any residual lime, and a final juice fraction results. This purified final juice fraction, containing only inseparable, less-harmful non-sugar impurities, is separated from the calcium carbonate and is ready for evaporative thickening and subsequent sucrose crystallization.

Alternatively, instead of transferring all of the first juice fraction containing the flocs to the first carbonation procedure, a separate carbonation procedure equivalent in operation to the first carbonation procedure can be provided for the first juice fraction only. When a separate carbonation procedure is employed, the first juice fraction (1) can be transferred to the separate carbonation procedure; (2) can be divided into two portions, with one pportion transferred to each of the first and separate carbonation procedures; or (3) can be divided into two portions, with one portion transferred to the first and/or separate carbonation procedure and the other portion mechanically filtered to remove the flocs and yield a floc-free juice fraction which then can be directed to the first carbonation procedure. After the separate carbonation procedure is completed, the resulting juice therefrom can be directed to the second carbonation procedure.

BRIEF DESCRIPTION OF THE DRAWINGS

An illustrative and presently preferred embodiment of the invention is shown in the accompanying drawing figure which is a schematic illustration of a beet juice purification system.

DETAILED DESCRIPTION OF A PREFERRED EMBODIMENT

The invention here described is a process for beet juice purification wherein prelimer flocs are removed with a first juice fraction from the major second juice fraction prior to main liming of the second juice fraction, and reintroduced along with the accompanying first juice fraction during first carbonation of the main-limed juice. The accompanying drawing figure is a schematic representation of the preferred process in which a juice purification system 10 is shown. As is illustrated, raw beet juice still containing mush is metered conventionally through a flowmeter 12 to a mesh screen means 14 whereby the mush is separated from the effluent diffusion juice. This effluent diffusion juice has essentially no beet tissue particles therein and comprises water, sugar and dissolved and colloidal non-sugar impurities. The juice then enters a conventional preliming chamber means 16 wherein lime is introduced by conventional meter means 11 from a lime dispenser vessel means 18 which is supplied by a tank means 19 to which milk of lime is supplied. It is to be understood that the terms "lime" and "milk of lime" as used throughout herein are meant to be synonymous. Recirculated carbonation sludge housed in a sludge dispenser vessel means 20 is likewise introduced by conventional meter means 13 into the preliming chamber means 16. The flowmeter 12 is in conventional electronic communiction with the respective meter means 11, 13, 17, as illustrated by the branched dotted line 33 in the drawing figure. The diffusion juice entering the preliming chamber means 16 generally comprises by weight of the initial beets about 105–106% water, 16–17% sugar, and 2.5–2.7% various dissolved non-sugar impurities. Progressive preliming as known in the art occurs within the preliming chamber means 16 by addition of lime and recirculated carbonation sludge to gradually raise the pH of the juice from about 6.5 to about 11.6. This gradual increase of pH value allows certain of the protein non-sugars to reach their respective iso-electric points to thereby enable their flocculation. Upon completion of preliming, the objects of the invention are realized. Specifically, instead of directing the entire prelimed juice content to main liming, the entire content is directed to a gravity settler tank means 22 wherein non-sugar flocs formed during preliming settle to the bottom while a major portion of resultant floc-free juice overflows to a cold main liming chamber means 24. The settled flocs are then transferred to a tank means 26, and are contained within a minor first juice fraction which naturally accompanies the flocs. As earlier noted, certain of the flocs formed during preliming are sensitive and can be destroyed by harsh chemical or mechanical treatment. Such destruction results in a loss of efficiency of non-sugar separation and therefore emphasizes the desirability of floc removal immediately after preliming. However, it is also recognized that a minor, yet significant, quantity of beneficial juice accompanies the flocs when they are separated from the major second fraction of the juice after preliming. It is therefore desirable to reclaim this floc-accompanying first juice fraction and simultaneously maintain the integrity of the flocs therewith. The present novel process accomplishes this reclamation by transferring preferably all of the flocs and accompanying first juice fraction dirctly to a conventional first carbonation chamber means 28 where the earier-produced and subsequently-treated floc-free second juice fraction likewise arrives. Because of the sensitivity of certain of the flocs to mechanical degradation, special and relatively gentle pumping means such as a volumetric pump means 30 is preferably employed to ensure against mechanically-induced flocculation loss. The so-transferred composition is then joined in the first carbonation chamber means 28 by the earlier-separated and subsequently-treated floc-free second juice fraction for further processing as described later.

Subsequent treatment of the floc-free second juice fraction collected after preliming and floc separation therefrom first includes cold main liming at ambient temperature in a cold main liming chamber means 24 as known in the art. The temperature is generally between 30°–40° C., and is coupled with continuous agitation to accomplish an intimate mix for a usual holding time of 10–20 minutes. Lime from a lime dispenser vessel means 15 is added by conventional meter means 17 through a proportional feeder means 21 to the chamber means 24 to increase the pH to a value over about 12.6 and thereby cause degradation of non-sugar impurities which are degradable at such lower temperatures. Other non-sugar impurities are decomposed in hot temperatures. Thus, after cold main liming, the limed juice is pumped by a conventional pump means 25 through a conventional heater means 34 and subsequently to a hot main liming chamber means 36. The heater means 34 heats the juice to about 80°–90° C., and it then is likewise continuously agitated and held in the hot main liming chamber means 36 for 10–20 minutes to thereby allow decomposition of the non-sugars which are sensitive to higher temperatures. Sufficient additional lime is added to maintain the pH value above about 12.6. Upon completion of main liming, the resulting limed juice is transferred to the first carbonation chamber means 28 and joined with the prelimer flocs and accompanying frrst juice fraction as earlier described for simultaneous subsequent purification treatment as now will be described.

Sufficient carbon dioxide gas is introduced into the first carbonation chamber means 28 where it reacts with about 95% of the lime (calcium hydroxide) from the preliming and main liming steps to produce a large volume of calcium carbonate fine precipitate. As is known, this precipitate adsorbs some still-dissolved non-sugars, and also acts as a filter aid. In addition, and in accord with the present invention, the calcium carbonate precipitate also effectively insulates the non-sugar flocs produced during preliming and delivered directly to the first carbonation chamber means 28 by creating permanent calcium carbonate scales around each floc particle. These created scales are very surface active and therefore attract additional mostly-dissolved non-sugars and colorants to thereby further promote juice purification. Simultaneously, of course, the first juice fraction accompanying the earlier-separated preliming flocs is reclaimed to thereby reduce a potential loss of a valuable sugar source.

Following the first carbonation step, the resultant juice is conveyed to a conventional degassing chamber means 38 where excess carbon dioxide is removed, and then to a conventional sludge thickener tank means 40. Clear juice therefrom is transferred to a juice collection tank means 42, and thence pumped by a conventional pump means 27 first to a second heater means 44 whereby juice temperature is raised to a temperature immediately below its boiling point, and then to a second carbonation chamber means 46 where additional carbon dioxide is introduced for removal of any residual lime, and finally to a filter means 48, all as known in the art. The resultant filtered purified thin juice is then ready for evaporative thickening and sucrose crystallization. Carbonation sludge from the sludge thickener tank means 40 is conveyed to a sludge collection tank means 50 as known in the art from which approximately one-third is directed by a conventional pump means 29 for recirculation in the preliming step. The remaining carbonation sludge is pumped by conventional pump means 31 from the tank means 50 and filtered through a filter means 52. Filtrate therefrom is directed to the juice collection tank means 42 for subsequent heating, second carbonation and filtration as above described for additional juice reclamation, while filtered sludge therefrom is de-sweetened by means of a water wash through the filter means 52 and thereafter is discarded.

Alternatively, instead of transferring all of the first juice fraction directly to the first carbonation chamber means 28, three other choices can be followed. First, all of the first juice fraction can be transferred directly to a separate carbonation chamber means 54 where treatment is equivalent to that in the first or second carbonation chamber means 28 and 46. That is, sufficient carbon dioxide gas is introduced into the separate carbonation chamber where it reacts with about 95% of the lime present from the preliming step to produce calcium carbonate fine precipitate which effectively insulates the non-sugar flocs as described above. Secondly, the first juice fraction can be divided into two portions, with one portion transferred to each of the first and separate carbonation chamber means 28, 54. Thirdly, the first juice fraction can be divided into two portions, with one portion transferred to either of the first or separate carbonation chamber means, 28, 54 or to both, and the other portion filtered to remove the flocs therefrom and yield a floc-free juice fraction which then is directed to the first carbonation chamber means 28 for continued processing as described above. Juice from the separate carbonation chamber means 54 is directed to the degassing chamber means 38 for subsequent treatment thereafter as described above.

EXAMPLE

The example which follows employs the inventive process here described in a typical factory operation. It is to be understood that the procsss is continuous in conventional production settings such as that now exemplified. For this reason, all quantities of materials recited are quantities per hour based on a 24-hour period of operation for 100 tons of beets.

After directing a quantity of raw diffusion juice through the flow meter 12 and mesh screen means 14, about 5.20 tons of effluent diffusion juice enters the preliming chamber means 16 into which is also introduced about 0.08 tons milk of lime (30% calcium hydroxide aqueuus solution) from the lime dispenser vessel means 18 and about 0.50 tons of recirculated carbonation sludge from the sludge dispenser vessel means 20. Respective conventional meter means 11, 13, in conventional electronic communication with the flowmeter 12, control the quantities of lime and sludge so introduced in accord with the amount of diffusion juice passing through the flowmeter 12 to thereby gradually raise the pH of the juice within the reliming chamber means 16 from about 6.5 to about 11.6 and enable flocculation of certain of the protein non-sugars in the juice, as known in the art. Upon completion of preliming, the resultant prelimed juice (about 5.82 tons) is transferred to the gravity settler tank means 22 where the non-sugar flocs formed during preliming settle to the bottom while a major portion (about 5.00 tons) of resultant floc-free juice overflows to the cold main liming chamber means 24. The settled flocs and accompanying first juice fraction, a total quantity of about 0.82 tons, are transferred to a tank menns 26 and subsequently pumped by a volumetric pump means 30 directly to the first carbonation chamber means 28.

To the floc-free second juice fraction which overflowed into the cold main liming chamber means 24 is added about 0.15 tons milk of lime from the dispenser vessel means 15 through the proportional feeder means 21. Such lime addition raises the pH to above about 12.6. Inside the cold main liming chamber means 24 is a conventional rotating propeller (not shown) which provides continuous agitation to form an intimate juice-and-lime mixture. Such agitation continues for a usual holding time of 10–20 minutes or until essentially all of those non-sugar impurities which are degradable without heat application are so degraded by the lime. The usual temperature during cold main liming is generally between 30°–40° C.

After cold main liming, the limed juice is pumped by the pump means 25 through the heater means 34, which raises the temperature of the juice to about 80°–90° C., hot main liming chamber means 36 to which is added about 0.16 tons milk of lime through the proportional feeder means 21. Such lime addition maintains the pH at above about 12.6. Inside the hot main liming chamber means 36 is a conventional rotating propeller (not shown) which continuous agitation to form an intimate juice-and-lime mixture. Agitation continues for a usual holding time of 10–20 minutes or until essentially all of those non-sugar impurities which degrade at elevated temperature are so degraded by the lime.

Upon completion of the main liming procedure, the resultant second juice fraction is transferred to the first carbonation chamber means 28 and joined with the prelimer flocs and accompanying first juice fraction as earlier described for simultaneous subsequent purification treatment. The total amount of juice entering the chamber means 28 is about 5.82 tons to which is added about 0.17 tons carbon dioxide gas. The carbon dioxide reacts with the lime to yield calcium carbonate fine precipitate. This precipitate adsorbs some still-dissolved non-sugars, and also effectively insulates the flocs transferred directly to the chamber means 28 by creating permanent calcium carbonate scales around each floc partccle. These scales are surface active and therefore adsorb additional mostly-dissolved non-sugar impurities and colorants. Simultaneously, the first juice fraction accompanying the flocs is reclaimed.

Following this first carbonation procedure, the resultant juice-and-calcium carbonate mixture is conveyed to a conventional degassing chamber means 38 where excess carbon dioxide is removed, and then to a conventional sludge thickener tank means 40. A yield of about 4.64 tons of clear juice therefrom is transferred to the juice collection tank means 42 and then pumped to a second heater means 44 where the juice temperature is raised to a temperature immediately below its boiling point. At an altitude of about 5,000 feet, this temperature is about 92° C. After heating, the juice is transferred to the second carbonation chamber means and 0.05 tons of carbon dioxide is introduced for reaction with residual lime. The juice is then filtered and is ready for evaporative thickening and sucrose crystallization as known in the art.

Concurrent with the above is the conveyance of carbonation sludge produced in the sludge thickener tank means 40 to the sludge collection tank means 50. The amount of sludge so transferred is about 1.67 tons, and about 0.5 tons thereof is directed by the pump means 29 for recirculation use in the preliming step. The remaining sludge, about 1.17 tons, is pumped from the tank means 50 for filtration through the filter means 52. Filtrate therefrom totalling about 0.75 tons is directed to the juice collection tank means 42 fo subsequent heating, second carbonation and filtration as described above to produce additional juice product. The remainder of the sludge, about 0.42 tons, is de-sweetened by means of a water wash and then discarded. The final yield of purified juice for the entire operation as described above is approximately 5.39 tons.

As will be recognized by a skilled artisan from the foregoing description, the present inventive process provides for (1) the separation of non-sugar flocs from the major juice fraction prior to main liming; (2) the maintenance of these separated flocs in a flocculated configuration whereby the non-sugar impurities so collected do not re-dissolve in the juice; and (3) the reclamation of a minor, yet significant, juice fraction which naturally accompanies the separated flocs by re-uniting the main limed major juice fraction with at least a portion, and preferably all, of the flocs and accompanying minor juice fraction during the first carbonation procedure.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A process for the removal of non-sugar impurities from beet diffusion juice having essentially no beet tissue particles therein and comprising water, sugar, and dissolved and colloidal non-sugar impurities, said process comprising the steps of:

(a) subjecting the diffusion juice to a progressive preliming procedure wherein lime and carbonation sludge are added to gradually increase the pH of the juice to about 11.6 to thereby produce a limed first juice fraction containing non-sugar flocs produced from non-sugar impurities which so flocculate and a limed second juice fraction which is floc-free;

(b) separating the first juice fraction containing the non-sugar flocs from the second juice fraction;

(c) subjecting the second juice fraction to a main liming procedure wherein lime is added to the second juice fraction and continuously intimately mixed therewith at ambient temperature to increase the pH thereof to above about 12.6 and wherein the resultant mixture is maintained for a period of time sufficient to degrade non-sugar impurities which are degradable at said temperature;

(d) heating with continuous intimate mixing thereof the mixture of (c) to about 80°-90° C. and maintaining said mixture for a period time sufficient to degrade non-sugar impurities which are degradable at said temperature;

(e) uniting without substantial mechanical or chemical degradation at least a portion of the first juice fraction containing at least a portion of the non-sugar flocs with the resulting second juice fraction of (d) in a first carbonation procedure wherein carbon dioxide gas is introduced in a quantity sufficient to react with at least about 95% of lime present in the first and second juice fractions to thereby produce a single juice fraction and calcium carbonate precipitate which adsorbs certain remaining disolved non-sugar impurities which are so adsorbable and which insulates the non-sugar flocs by creating permanent calcium carbonate scales around each floc particle;

(f) separating the single juice fraction of (e) and further treating said juice fraction in a second carbonation procedure wherein the juice is heated to a temperature immediately below the boiling point of the juice and carbon dioxide gas is introduced in a quantity sufficient to react with substantially all lime there present to thereby produce calcium carbonate precipitate and a final juice fraction; and (g) separating the final juice fraction of (f) from the calcium carbonate precipitate.

2. The process as claimed in claim 1 wherein the ambient temperature of the main liming procedure is from about 30° C. to about 40° C.

3. The process as claimed in claim 1 wherein all of the first juice fraction containing all of the non-sugar flocs is united with the second juice fraction of (d) in the first carbonation procedure.

4. The process as claimed in claim 1 wherein a portion of the first juice fraction containing a portion of the non-sugar flocs is united with the second juice fraction of (d) in the first carbonation procedure, and wherein the remaining first juice fraction containing the remaining non-sugar flocs is mechanically filtered to yield a floc-free juice portion which is united with the second juice fraction of (d) in the first carbonation procedure.

5. A process for the removal of non-sugar impurities from beet diffusion juice having essentially no beet tissue particles therein and comprising water, sugar, and dissolved and colloidal non-sugar impurities, said process comprising the steps of:

(a) subjecting the diffusion juice to a progressive preliming procedure wherein lime and carbonation sludge are added to gradually increase the pH of the juice to about 11.6 to thereby produce a limed first juice fraction containing non-sugar flocs produced from non-sugar impurities which so flocculate and a limed second juice fraction which is floc-free;

(b) separating the first juice fraction containing the non-sugar flocs from the second juice fraction;

(c) subjecting the second juice fraction to a main liming procedure wherein lime is added to the second juice fraction and continuously intimately mixed therewith at ambient temperature to increase the pH thereof to above about 12.6 and wherein the resultant mixture is maintained for a period of time sufficient to degrade non-sugar impurities which are degradable at said temperature;

(d) heating with continuous intimate mixing thereof the mixture of (c) to about 80°-90° C. and maintaining said mixture for a period time sufficient to degrade non-sugar impurities which are degradable at said temperature;

(e) subjecting the resulting second juice fraction of (d) to a first carbonation procedure wherein carbon dioxide gas is introduced in a quantity sufficient to react with at least about 95% of lime present in the second juice fraction to thereby produce a second juice fraction and calcium carbonate precipitate which adsorbs certain remaining dissolved non-sugar impurities which are so adsorbable;

(f) subjecting at least a portion of the first juice fraction containing at least a portion of the non-sugar flocs to a separate carbonation procedure wherein carbon dioxide gas is introduced in a quantity sufficient to react with at least about 95% of lime present in the first juice fraction to thereby produce a first juice fraction and calcium carbonate precipitate which adsorbs certain remaining dissolved non-sugar impurities which are so adsorbable and which insulates the non-sugar flocs by creating permanent calcium carbonate scales around each floc particle;

(g) separating out the juice fraction of (e) and the juice fraction of (f) and uniting the resulting juice fractions of (e) and (f) to form a single juice fraction and further treating said single juice fraction in a second carbonation procedure wherein the juice is heated to a temperature immediately below the boiling point of the juice and carbon dioxide gas is introduced in a quantity sufficient to react with substantially all lime there present to thereby produce calcium carbonate precipitate and a final juice fraction; and (h) separating the final juice fraction of (g) from the calcium carbonate precipitate.

6. The process as claimed in claim 5 wherein a portion of the first juice fraction containing a portion of the non-sugar flocs is subjected to the separate carbonation procedure and wherein the remainder of the first juice fraction containing the remainder of the non-sugar flocs is mechanically filtered to yield a floc-free juice fraction which is united with the second juice fraction in the first carbonation procedure.

7. The process as claimed in claim 5 wherein a portion of the first juice fraction containing a portion of the non-sugar flocs is subjected to the separate carbonation procedure and wherein the remainder of the first juice fraction containing the remainder of the non-sugar flocs is united without subsantial mechanical or chemical degradation with the resulting second juice fraction of (d) in the first carbonation procedure wherein the calcium carbonate precipitate insulates the non-sugar flocs by creating permanent calcium carbonate scales around each floc particle.

8. The process as claimed in claim 5 wherein the ambient temperature of the main liming procedure if from about 30° C. to about 40° C.

9. The process as claimed in claim 5 wherein all of the first juice fraction containing all of the non-sugar flocs is subjected to the second carbonation procedure.

10. A process for isolating and separating ceertain non-sugar impurities present in beet diffusion juice having esentially no beet tissue particles therein and comprising water, sugar, and dissolved and colloidal non-sugar impurities, said certain non-sugar impurities comprising those which flocculate upon subjection to a progressive preliming procedure, said process comprising the steps of:

(a) subjecting the diffusion juice to a progessive preliming procedure wherein lime and carbonation sludge are added to gradually increase the pH of the juice to about 11.6 to thereby produce a limed first juice fraction containing non-sugar flocs produced from the certain non-sugar impurities which so flocculate and a limed second juice fraction which is floc-free;

(b) separating the first juice fraction containing the non-sugar flocs from the second juice fraction;

(c) subjecting the first juice fraction containing the non-sugar flocs to a carbonation procedure wherein carbon dioxide gas is introduced in a quantity sufficient to react with at least about 95% of the lime present in the first juice fraction to thereby produce calcium carbonate precipitate which insulates the non-sugar flocs by crating permanent calcium carbonate scales around each floc particle; and.

(d) separating therefrom the first juice fraction.

* * * * *

UNITED STATES PATENT AND TRADEMARK OFFICE
CERTIFICATE OF CORRECTION

PATENT NO. : 4,795,494
DATED : January 3, 1989
INVENTOR(S) : Laszlo Toth and Michael R. Conway It is certified that error appears in the above-identified patent and that said Letters Patent is hereby corrected as shown below:

Column 3, line 11, "pportion" should read --portion--.
Column 4, line 26, "earier" should read --earlier--.
Column 6, line 17, "aqueuus" should read --aqueous--;
line 25, "reliming" should read --preliming--;
line 36, "menns" should read --means--; and
line 56, before "hot", --and into the-- should have been added.
Column 7, line 11, "partccle" should read --particle--; and
line 41, "fo" should read --for--.

Claim 10, Column 10, line 38, "progessive" should read --progressive-- and
line 54, "crating" should read --creating--.

Signed and Sealed this

Second Day of May, 1989

*Attest:*

DONALD J. QUIGG

*Attesting Officer*

*Commissioner of Patents and Trademarks*